US012736522B2

(12) United States Patent
Atsalakis

(10) Patent No.: US 12,736,522 B2
(45) Date of Patent: Sep. 15, 2026

(54) BREATH ANALYSIS DEVICE

(71) Applicant: PNOĒ Inc., Malden, MA (US)

(72) Inventor: Apostolos Atsalakis, Malden, MA (US)

(73) Assignee: PNOE Inc., Malden, MA (US)

( * ) Notice: Subject to any disclaimer, the term of this patent is extended or adjusted under 35 U.S.C. 154(b) by 0 days.

(21) Appl. No.: 16/092,988

(22) PCT Filed: Apr. 11, 2017

(86) PCT No.: PCT/US2017/026979
§ 371 (c)(1),
(2) Date: Oct. 11, 2018

(87) PCT Pub. No.: WO2017/180605
PCT Pub. Date: Oct. 19, 2017

(65) Prior Publication Data

US 2019/0120821 A1 Apr. 25, 2019

(30) Foreign Application Priority Data

Apr. 12, 2016 (GB) .................................... 1606292
Feb. 21, 2017 (EP) .................................... 17386006

(51) Int. Cl.
*G01N 33/497* (2006.01)
*A61B 5/08* (2006.01)
*A61B 5/083* (2006.01)
*A61B 5/087* (2006.01)
*A61B 5/097* (2006.01)

(52) U.S. Cl.
CPC ......... *G01N 33/497* (2013.01); *A61B 5/0803* (2013.01); *A61B 5/0833* (2013.01); *A61B 5/0836* (2013.01); *A61B 5/087* (2013.01); *A61B 5/097* (2013.01)

(58) Field of Classification Search
CPC .. G01N 33/497; A61B 5/0803; A61B 5/0833; A61B 5/0836; A61B 5/087; A61B 5/097
See application file for complete search history.

(56) References Cited

U.S. PATENT DOCUMENTS 4,368,740 A 1/1983 Binder
5,072,737 A 12/1991 Goulding
(Continued)

FOREIGN PATENT DOCUMENTS

CN 105277586 A 1/2016
EP 1 764 036 A1 3/2007
(Continued)

OTHER PUBLICATIONS

Supplementary European Search Report mailed Apr. 10, 2019, in reference to co-pending United States Patent Application No. PCT/US2017/026979 filed on Apr. 11, 2017.
(Continued)

*Primary Examiner* — Tse W Chen
*Assistant Examiner* — Joseph A Tombers
(74) *Attorney, Agent, or Firm* — Dinsmore & Shohl LLP

(57) ABSTRACT

Provided herein is a portable breath analysis device for analysing breath of a subject to identify levels of gases such as oxygen and carbon dioxide. The device fmds use in, for example, monitoring the health of subjects. Also provided herein are methods of analysing breath of a subject using the device.

17 Claims, 5 Drawing Sheets

(56) References Cited

U.S. PATENT DOCUMENTS

| | | | | |
|---|---|---|---|---|
| 5,284,054 | A * | 2/1994 | Loebach | G01N 33/497 73/23.3 |
| 5,363,857 | A | 11/1994 | Howard | |
| 10,561,863 | B1 * | 2/2020 | Dashevsky | A61B 5/01 |
| 2003/0065274 | A1 * | 4/2003 | Mault | A61B 5/087 600/531 |
| 2003/0192542 | A1 | 10/2003 | Isaza | |
| 2004/0210154 | A1 | 10/2004 | Kline | |
| 2007/0123792 | A1 | 5/2007 | Kline | |
| 2007/0191726 | A1 | 8/2007 | Harnoncourt et al. | |
| 2008/0161710 | A1 * | 7/2008 | Gunneson | A61M 16/0816 600/532 |
| 2009/0038615 | A1 * | 2/2009 | Bradley | A61B 5/097 128/204.17 |
| 2010/0268106 | A1 * | 10/2010 | Johnson | A61B 5/097 600/532 |
| 2014/0128691 | A1 | 5/2014 | Olivier | |
| 2014/0234172 | A1 * | 8/2014 | Burgi | G01N 33/4972 422/84 |
| 2014/0235961 | A1 * | 8/2014 | Brugnoli | G01N 19/10 600/301 |
| 2014/0276100 | A1 * | 9/2014 | Satterfield | A61B 5/7271 600/476 |
| 2014/0336523 | A1 * | 11/2014 | Brix | A61M 16/00 600/531 |
| 2015/0250408 | A1 * | 9/2015 | Ssenyange | G01N 33/0037 600/532 |
| 2015/0314101 | A1 | 11/2015 | Acker et al. | |
| 2016/0255878 | A1 * | 9/2016 | Huang | A24F 40/51 |
| 2017/0065208 | A1 * | 3/2017 | Furusaki | G01N 27/4067 |
| 2017/0245795 | A1 * | 8/2017 | Norlien | A61M 16/06 |

FOREIGN PATENT DOCUMENTS

| | | | |
|---|---|---|---|
| JP | 2002535024 | A | 10/2002 |
| JP | 2007167170 | A | 7/2007 |
| JP | 2008051744 | A | 3/2008 |
| JP | 2014021101 | A | 2/2014 |
| JP | 2014532523 | A | 12/2014 |
| WO | 2000042908 | | 7/2000 |
| WO | 2004/041084 | A1 | 5/2004 |
| WO | 2009125225 | A1 | 10/2009 |
| WO | 201307712 | A1 | 5/2013 |
| WO | 2014052741 | A1 | 4/2014 |
| WO | 2015031818 | A1 | 3/2015 |
| WO | 2015191558 | A1 | 12/2015 |

OTHER PUBLICATIONS

International Search Report mailed Jun. 27, 2017, in reference to co-pending United States Patent Application No. PCT/US2017/026979 filed on Apr. 11, 2017.

K.H.Kim, “A Review of Breath Analysis for Diagnosis of Human Health,” Trends in Analytical Chemistry, vol. 33, 2012.

George G. Guilbault, “Non-invasive biosensors in clinical analysis,” Elsevier Science Ltd., 1995.

Wei Ma, “Analysis of human breath with micro extraction techniques and continuous monitoring of carbon dioxide concentration,” Analytical and Bioanalytical Chemistry, 2006.

Examination Report in relation to corresponding European patent family member Application No. 17782964.5 filed Apr. 11, 2017.

* cited by examiner

BREATH ANALYSIS DEVICE

CROSS REFERENCE TO RELATED APPLICATION

This application claims the benefit to EP17386006.5 filed Feb. 21, 2017 and GB1606292.9 filed Apr. 12, 2016, which is incorporated by reference in its entirety.

FIELD OF THE INVENTION

This invention relates to a device for measurement of breath. In particular, but not exclusively, the present invention relates to a portable breath analysis device suitable for use in indirect calorimetry. The invention also relates to a method of analysing a subject's breath.

BACKGROUND OF THE INVENTION

Breath analysis has gained a lot of interest during recent years since it is a non-invasive technique that has many promising results. Since ancient times, physicians have been aware of the relationship between the odour of a person's breath and certain diseases. Since then it has been recognised that breath could give insight into physiological and pathophysiological processes of the human body (see, for example, W. Ma, W, Liu X and J. Pawliszyn, "Analysis of human breath with micro extraction techniques and continuous monitoring of carbon dioxide concentration", Analytical and Bioanalytical Chemistry, (2006)).

The human breath is a mixture of inorganic gases (NO, $CO_2$, CO, nitrogen), volatile organic compounds (VOCs) (isoprene, ethane, pentane, acetone) and other non-volatile substances (isoprostanes, peroxynitrine, cytokines). Generally, the components of human breath have endogenous and exogenous origins and an analysis of their composition can be related to the physiological processes that have taken place as well as to the pathways of ingestion or absorption (see K. Kim, J. Shamin and E. Kabir, "A review of breath analysis for diagnosis of human breath", Trends in Analytical Chemistry, (2012)). As a result, breath can be regarded as a fingerprint of the human health and its analysis has significant medical applications.

Generally, the advantages of breath analysis tests can be identified in their safety and non-invasive nature. The simplicity of breath analysis is particularly interesting for patients who have to monitor their health daily such as patients who are diabetic, have to monitor their urea etc. (G. Guilbault, G. Palleschi and G. Lubrano, "Non-invasive biosensors in clinical analysis", Biosensors and Bioelectronics, (1995)).

As a result, there is a great demand for hand-held devices that can help people monitor their health in a domestic environment. Moreover, one of the major goals of recent medicine is early detection that dramatically increases the chances of a successful treatment, and breath analysis can help in this.

Indirect calorimetry is used to measure the human metabolism by the amounts of $O_2$ and $CO_2$ that are found in the exhaled human breath. A human's energy expenditure is divided into resting metabolic rate (RMR), physical activities and thermogenesis that is induced by food intake. RMR represents the largest percentage of the total energy expenditure (>75%) (W. McArdle, F. Katch and V. Katch, "Exercise physiology: nutrition, energy and human performance", $7^{th}$ ed. Lippincott Williams & Wilkins, (2010)). Determining RMR has improved our understanding of the pathophysiology of obesity and it can help patients undergoing weight loss due to malnutrition, especially in intensive care units. Currently RMR is determined by whole body respiratory chambers and metabolic carts but such methods are costly and require trained technicians. Moreover, mathematical models that have been developed for the prediction of RMR fail by a rate of 50% to 70% and are often found to be inaccurate in cases of obesity, anorexia nervosa and other illnesses. Thus, there is a need for an inexpensive, handheld and easy to use device to perform indirect calorimetry measurements and determine accurately the RMR of a person.

Apart from the numerous fitness applications, a hand-held breathalyser that measures the human metabolism also finds use in controlling the diet of obese individuals. Obesity is currently a major problem and a 2014 report by the Health & Social Information Centre reported that only 32.1% of men and 40.6% of women in England have a normal Body Mass Index (BMI) (Statistics on Obesity, Physical Activity and Diet, Health & Social Care Information Center, (2014)). Moreover, obesity is related to type II diabetes, coronary heart disease, different types of cancer (breast cancer, bowel cancer etc.) and stroke according to a report of the National Health Service (http://www.nhs.uk/conditions/obesity/Pages/Introduction.aspx accessed on 6 Apr. 2016).

Currently there are just two hand-held breathalysers on the market, sold under the trade names MedGem (by Microlife Medical Home Solutions Inc. of 2801 Youngfield St., Suite 241 Golden, CO 80401, USA) and Breezing (by Breezing, Co. of 2601 N 3rd St, Suite 108, Phoenix, AZ, 85004). The MedGem device measures only the exhaled oxygen in the breath and assumes that the expired carbon dioxide has a constant ratio of 0.85 when compared to oxygen. That of course, is only an assumption and, as it is very often not a correct assumption, it leads to erroneous measurements. The MedGem device is unable to measure both $O_2$ and $CO_2$ on a breath-by-breath basis in order to deliver the required accuracy. In fact, the ratio of exhaled carbon dioxide to exhaled oxygen is defined as the respiratory quotient (RQ) and varies between 0.6 and 1.0. Based on the RQ measured, it can be determined whether the individual burns mainly fat (RQ=0.7), protein (RQ=0.8) or carbohydrates (RQ=1.0). The accuracy of the determination of the RQ is thus very important. The accurate determination of the RQ is a metric equally important to the measurement of the metabolism. Measuring both the RQ and the metabolism of an individual enables one to take a more holistic approach to the treatment of the user. Moreover, there are certain information that can be drawn from the RQ, such as the overfeeding or underfeeding of an individual, that the MedGem device is unable to track. Also, by measuring only the exhaled oxygen and neglecting the sensing of the carbon dioxide, the MedGem device cannot determine whether protein, fat or carbohydrates have been metabolised by an individual. Moreover, RQ changes significantly in many medical cases of pulmonary diseases (COPD, asthma etc.) and this restricts MedGem from being used widely in a medical environment.

The second device that is currently available in the market place is sold under the trade name Breezing. This device senses both oxygen and carbon dioxide. It uses consumable sensors which is disadvantageous in many settings. It means that each test requires a consumable sensor that costs approximately 5$ (USD). Use of disposable parts is inconvenient and costly. There are many cases in which an individual may need to measure his metabolism/RER numerous times during the day and this of course increases significantly the cost with the Breezing device. Moreover, in clinical settings the cost of such a device again increases significantly because each patient's measurement requires the usage of costly consumables.

Despite the burning need to create a low-cost, hand-held breathalyzer that measures both the human metabolism and the respiratory quotient (RQ) without using consumable components, there is currently no device available with such a specification. The invention described in this patent application solves this problem and is able to measure the metabolism with a gold-standard accuracy.

SUMMARY OF THE INVENTION

In a first aspect, the present invention provides a portable breath analysis device comprising a primary gas flow pathway for passage of exhaled breath from an inlet to an outlet a secondary gas flow pathway branched from the primary pathway at a branching point between the inlet and the outlet, the secondary pathway also having an outlet; a flow sensor between the inlet of the primary pathway and the branching point or between the branching point and the outlet of the primary pathway and arranged to allow measurement of the gas flow in the primary pathway; an oxygen sensor; and a carbon dioxide sensor, wherein the oxygen sensor and the carbon dioxide sensor are arranged in the secondary pathway to take measurements of the exhaled breath in that pathway. The oxygen sensor the carbon dioxide sensor are arranged in the secondary pathway in sequence. They are in-line with each other.

In certain modes of use, the gas in the inhaled breath is also analysed; when inhaled gas is analysed, the flow of gas is reversed, and it passes from the outlet to the inlet.

The invention allows the precise measurement of the consumed oxygen and produced carbon dioxide via a fully portable and low-cost device. As both the oxygen consumption and carbon dioxide production are measured by the device, the respiratory quotient (RQ) that determines whether an individual metabolises fat, protein or carbohydrates can be accurately measured, rather than relying on assumptions for fixed values of the RQ. In a preferred embodiment, the device does not use consumables and that reduces the cost of running the device. The ability to measure oxygen and carbon dioxide production on a breath-by-breath basis is of great advantage compared to devices of the prior art, many of which used sampling chambers for collecting exhaled breath. Sampling chambers are inaccurate because the sample of the new breath is mixed with the remains of previous breaths. Moreover, the chamber approach is slower and struggles to deliver a breath-by-breath analysis. Sampling chambers which measure averaged values cannot draw conclusions about the profile of carbon dioxide and oxygen. Also, sampling chambers analyse only the exhaled breath. When only the exhaled breath is able to be analysed as with sampling chambers, the Haldane transformation needs to be taken into account and this increases possibly the error of the measurement.

In contrast, devices of the invention are able to track the oxygen profile, carbon dioxide profile and flow measurement on a breath-by-breath basis. An in-line arrangement of oxygen and carbon dioxide sensors is important for detecting the profiles of the oxygen, carbon dioxide and flow measurements. Such profiles obtained from a device of the invention are shown in FIG. 3. Such detection was not possible with the sampling chambers used in the prior-art. An in-line connection allows real-time measurements in contrast with the sampling chamber that averages the values and is unable to measure the profiles of the measurements. Generating the profile for the oxygen, carbon dioxide and flow on every breath allows the integration of those signals to generate precise measurements of the consumed oxygen and produced carbon dioxide. Devices of the present invention are also able to measure both exhaled and inhaled breath if desired, unlike sampling chamber devices of the prior art.

It has been found that an in-line connection as in the present invention offers substantial benefits when compared to side stream flow configurations that arrange sensors in a parallel formation, i.e. that have a branching on the side stream that separates the secondary flow into 2 or more sub streams each one feeding gas into a sensor. In a parallel configuration, the branching point can create substantial turbulence (especially at high flow rates in the secondary pathway) thus increasing the pressure variation and affecting the measurements of the sensors, which are often highly sensitive to pressure fluctuations. It has been found that use of an in-line arrangement of sensors mitigates these problems.

Preferably, the device is an indirect calorimeter. Indirect calorimetry is a useful tool for analysing the metabolism of a subject which may be useful for medical reasons, or for diet and lifestyle reasons. Indirect calorimeters have several medical applications in the assessment of diabetes, obesity, anorexia, cardiovascular diseases etc., but existing indirect calorimeters are bulky and cost approximately $30,000. The functioning of a device of the present invention as an indirect calorimeter is thus advantageous as it provides a portable, hand-held indirect calorimeter device that can be used by an individual in a domestic environment.

Whilst in some embodiments the device does not comprise a dehumidifying means, in other preferred embodiments the device may comprise a dehumidifying means. A dehumidifying means reduces the humidity of exhaled breath, which contains a lot of moisture, to reduce condensation on the sensors and thus enable accurate measurements by the sensors. The humidity of exhaled breath can also adversely affect the accuracy of sensor measurements aside from by causing condensation.

Inhaled breath has a low relative humidity whereas exhaled breath has a very high relative humidity, but it is desirable that this humidity difference does not affect measurement of the breath; inhaled and exhaled breath are preferably compared on the same basis. A dehumidifying means is useful in reducing the humidity of exhaled breath to ambient levels in order to provide the same humidity between exhaled and inhaled breath, which is beneficial for the accurate analysis of the breath. Unlike other indirect calorimeters that use a sampling chamber, the devices of the present invention which comprise a dehumidifying means have the significant advantage that humidity is controlled very precisely in both the inhalation and the exhalation of the user by use of a dehumidifying means in combination with the in-line arrangement of the sensors. Such an arrangement is advantageous compared to prior-art designs that instead use a sampling chamber, which suffer from condensation problems inside the chamber and on the sensors which limits significantly their accuracy.

The device may comprise a pump to draw a sample of exhaled breath along the secondary pathway. The presence of a pump helps to ensure a constant flow rate through the secondary pathway and across the sensors. Alternatively, the device may not comprise a pump, and the flow of gases through the sensors can be controlled by the dimensions and configuration of the gas flow pathways; for example, tubes of smaller diameter may be used along the gas flow pathways to reduce the flow rate of the exhaled breath as it passes through them. Regulation of the flow rate through the secondary pathway to a steady flow is desirable both to ensure accurate readings of the sensors and that the dehumidifying means functions efficiently.

In some embodiments, the device comprises a valve system located between the branching point and the oxygen and carbon dioxide sensors and partitioning the secondary pathway into an upstream portion between the branching point and the valve system and a downstream portion between the valve system and the outlet of the secondary pathway, wherein the components of the valve system are movable between at least a first position and a second position, and wherein: the valve system comprises a valve outlet; in the first position, the components of the valve system are arranged such that the upstream portion of the secondary pathway is in fluid connection with the downstream portion of the secondary pathway; and in the second position, the components of the valve system are arranged such that the upstream portion of the secondary pathway is in fluid connection with the valve outlet and not with the downstream portion of the secondary pathway. This valve system enables the device to operate in different "modes" depending on the breathing rate of the user, by allowing subsequent breaths to be measured by the sensors, or, for example, every second breath, every third breath etc. when the breathing rate is higher. In other embodiments the device does not comprise such a valve system and every breath is analysed by the device.

Preferably, the device comprises a microcontroller. The microcontroller carries out the data processing of the device, such as receiving the measurements from each of the sensors, determining the mode to be used from the flow sensor measurements, and controlling the valve system. The microcontroller may also power the pump.

The device may further comprise a one-way valve positioned between the inlet and the flow sensor, through which gas may pass in a direction from the inlet to the flow sensor only. Such a valve requires a user to breathe out through the mouth and in through the nose, and does not allow the user to inhale by way of the primary pathway, in situations where this is desirable.

The device may further comprise a humidity sensor. This allows measurements by the oxygen and carbon dioxide sensors to be compensated for changes in humidity. The device may further comprise a temperature sensor. This allows measurements by the oxygen and carbon dioxide sensors to be compensated for changes in temperature.

The device may further comprise a pressure sensor. This allows measurements by the oxygen and carbon dioxide sensors to be compensated for changes in pressure. The device may further comprise one or more further sensors. This allows the device to measure additional parameters that may be of interest. For example, the device may include a sensor of acetone, nitric oxide, sulphur compounds, pentane, ethanol and/or hydrocarbons. In particular, when a pentane and ethanol sensor are present, oxidative stress may be monitored.

The device may further comprise a sampling chamber positioned along the secondary pathway between the oxygen and carbon dioxide sensors and the outlet of the secondary pathway, or branched from the secondary pathway at any point along the secondary pathway. One or more further sensors may be in fluid connection with the interior of the sampling chamber, for analysing the collected breath. This embodiment combines the benefits of the in-line connection of oxygen and carbon-dioxide sensors discussed above (in particular the ability to conduct measurements on a breath-by-breath basis), which functions best with fast-response sensors, with the use of a sampling chamber which allows the use of slower response sensors that cannot be connected in line. Preferably, the device comprises a communication means for communication between the microcontroller and a mobile phone or other device. This allows the user to review the collected data in a convenient and user-friendly manner.

According to a second aspect of the invention, there is provided a portable breath analysis device comprising: a primary gas flow pathway for passage of exhaled breath from an inlet to an outlet; a secondary gas flow pathway branched from the primary pathway at a branching point between the inlet and the outlet, the secondary pathway also having an outlet; a flow sensor between the inlet of the primary pathway and the branching point or between the branching point and the outlet of the primary pathway and arranged to allow measurement of the gas flow in the primary pathway; at least one sensor for a gas; and a valve system movable between at least a first position and a second position. The valve system located between the branching point and the at least one sensor and partitioning the secondary pathway into an upstream portion between the branching point and the valve system and a downstream portion between the valve system and outlet of the secondary pathway, wherein the components of the valve system are movable between at least a first position and a second position, and wherein: the valve system comprises a valve outlet; in the first position, the components of the valve system are arranged such that upstream portion of the secondary pathway is in fluid connection with the downstream portion of the secondary pathway; and in the second position, the components of the valve system are arranged such that the upstream portion of the secondary pathway is in fluid connection with the valve outlet and not with the downstream portion of the secondary pathway. This provides a portable device which may operate in various modes including breath-by-breath, for the analysis of the desired parameters of exhaled breath.

The device of the second aspect of the invention may comprise a carbon dioxide sensor. The device may also or alternatively comprise an oxygen sensor. Preferably, the device comprises both a carbon dioxide sensor and an oxygen sensor arranged in-line and is preferably indirect calorimeter, to allow a user to use the device for the monitoring of their metabolism.

As with the device of the first aspect, whilst in some embodiments the device of the second aspect may not comprise a dehumidifying means, preferably the device of the second aspect may also comprise a dehumidifying means, e.g. positioned in the primary or secondary pathway between the inlet and the at least one sensor. A dehumidifying means reduces the humidity of exhaled breath, which contains a lot of moisture, to reduce condensation on the sensors and thus enable accurate measurements by the sensors.

The device may comprise a pump to draw a sample of exhaled breath along the secondary pathway. The presence of a pump helps to ensure a constant flow rate through the secondary pathway and across the sensors. Alternatively, the device may not comprise a pump and the flow of gases through the gas sensor can be set by the dimensions and configuration of the gas flow pathways.

The device may further comprise a one-way valve through which gas may pass in a downstream direction only, positioned in the primary pathway and upstream of the flow sensor. Such a valve requires a user to breathe out through the mouth and in through the nose, and does not allow the user to inhale by way of the primary pathway, in situations where this is desirable.

The device may further comprise a humidity sensor. This will allow measurements by the oxygen and carbon dioxide sensors to be compensated for changes in humidity. The device may further comprise a temperature sensor. This will allow measurements by the oxygen and carbon dioxide sensors to be compensated for changes in temperature.

The device may further comprise a pressure sensor. This will allow measurements by the oxygen and carbon dioxide sensors to be compensated for changes in pressure. The device may further comprise one or more further sensors. This will allow the device to measure additional parameters that may be of interest. For example, the device may include a sensor of acetone, nitric oxide, sulphur compounds, pentane, ethanol and/or hydrocarbons. In particular, when a pentane and ethanol sensor are present, oxidative stress may be monitored.

The device of the second aspect may further comprise a sampling chamber positioned along the secondary pathway between the at least one sensor and the outlet of the secondary pathway, or branched from the secondary pathway at any point along the secondary pathway. One or more further sensors may be in fluid connection with the interior of the sampling chamber, for analysing the collected breath. This embodiment combines use of fast response time sensors which can measure on a breath-by-breath basis (such as carbon dioxide and oxygen sensor, as discussed above) with the use of a sampling chamber which allows the use of slower response sensors that cannot measure on a breath-by-breath basis.

Preferably, the device comprises a communication means for communication between the microcontroller and a mobile phone or other device. This allows the user to review the collected data in a convenient and user-friendly manner.

According to a third aspect of the invention, there is provided a method of analysing exhaled breath of a subject comprising the step of the subject breathing into a breath analysis device, wherein the device comprises: a primary gas flow pathway for passage of exhaled breath from an inlet to an outlet; a secondary gas flow pathway branched from the primary pathway at a branching point between the inlet and the outlet, the secondary pathway also having an outlet; a flow sensor between the inlet of the primary pathway and the branching point or between the branching point and the outlet of the primary pathway and arranged to allow measurement of the gas flow in the primary pathway; an oxygen sensor; and a carbon dioxide sensor, wherein the oxygen sensor and the carbon dioxide sensor are arranged in-line in the secondary pathway to take measurements of the exhaled breath in that pathway.

According to a fourth aspect, there is provided a method of analysing exhaled breath of a subject comprising the step of the subject breathing into a breath analysis device, wherein the device comprises a primary gas flow pathway for passage of exhaled breath from an inlet to an outlet; a secondary gas flow pathway branched from the primary pathway at a branching point between the inlet and the outlet, the secondary pathway also having an outlet; a flow sensor between the inlet of the primary pathway and the branching point or between the branching point and the outlet of the primary pathway and arranged to allow measurement of the gas flow in the primary pathway; at least one sensor for a gas; a valve system located between the branching point and the at least one sensor and partitioning the secondary pathway into an upstream portion between the branching point and the valve system and a downstream portion between the valve system and outlet of the secondary pathway, wherein the components of the valve system are movable between at least a first position and a second position, and wherein: the valve system comprises a valve outlet; in the first position, the components of the valve system are arranged such that the upstream portion of the secondary pathway is in fluid connection with the downstream portion of the secondary pathway; and in the second position, the components of the valve system are arranged such that the upstream portion of the secondary pathway is in fluid connection with the valve outlet and not with the downstream portion of the secondary pathway.

It will of course be appreciated that features described in relation to one aspect of the present invention may be incorporated into other aspects of the invention. For example, the first aspect of the invention may incorporate any of the features described with reference to the second or third aspects of the invention and vice versa.

DETAILED DESCRIPTION

Figure 1:
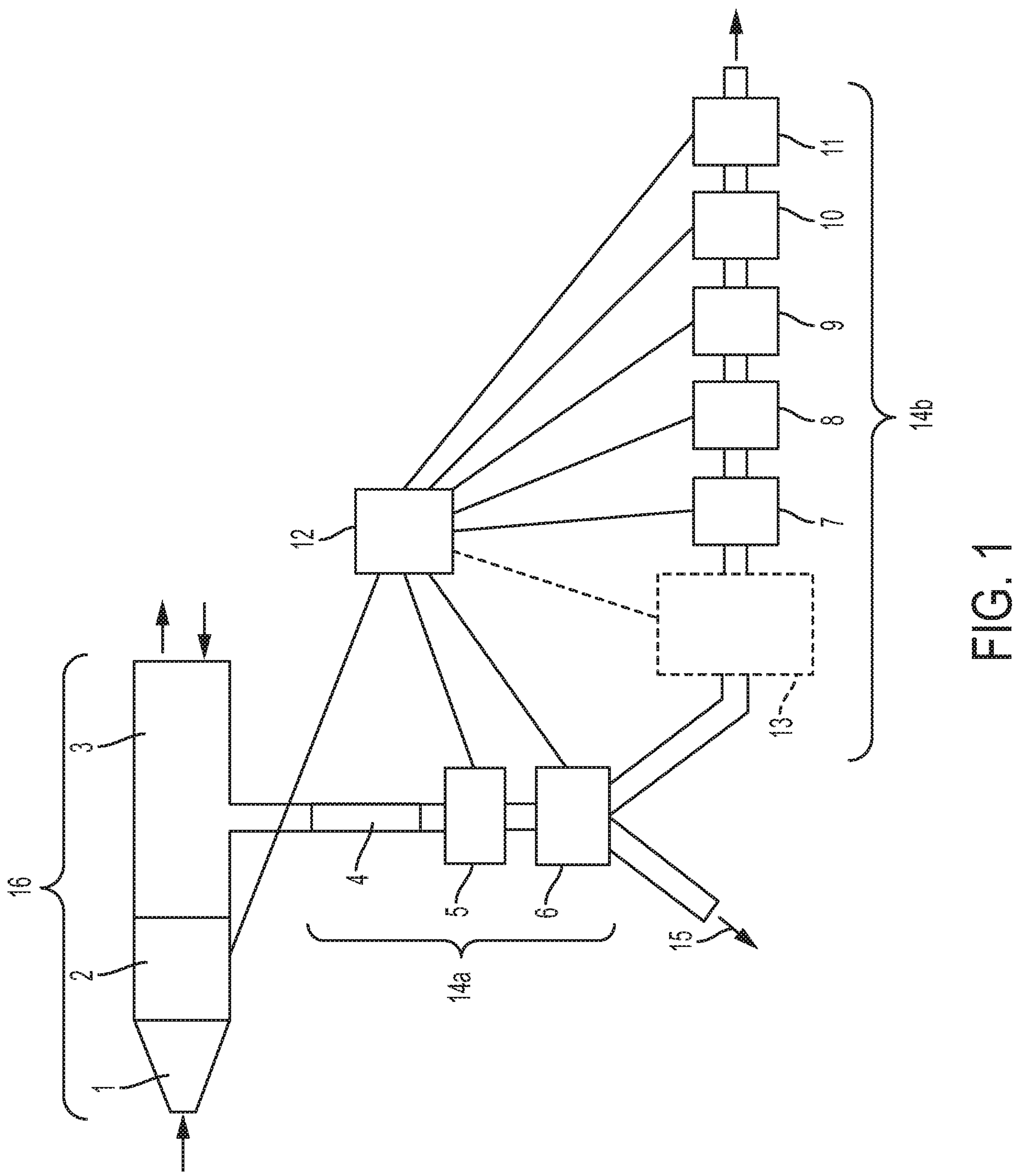
FIG. 1 shows a schematic diagram of an embodiment of the invention.

According to a first aspect of the invention, the breath analysis device comprises a primary gas flow pathway for passage of exhaled breath from an inlet to an outlet.

When using the device, a subject breathes into the device at the inlet of the primary pathway. Preferably, the entire exhaled breath of the user is led to the primary pathway and the primary pathway is filled with the exhaled breath when the user exhales the device.

In some embodiments of the invention, the primary pathway may also be used for the passage of air to be inhaled; as the subject inhales, ambient air is drawn in the reverse direction to that of the exhaled breath, through the outlet of the primary pathway towards the subject. In alternative embodiments, the user does not inhale through the mouth when using the device, and so ambient air to be inhaled does not pass through the primary pathway to the user. The device could operate either analysing only the exhaled breath or both the inhaled/exhaled breath.

To facilitate the user exhaling entirely into the device, the primary pathway may include at the inlet a facemask or a mouthpiece, for example.

The device comprises a secondary gas flow pathway which is branched from the primary pathway at a branching point between the inlet and the outlet, the secondary pathway also having an outlet. This allows the fragmental sampling of each breath. When a subject exhales into the device, the exhaled breath fills the primary pathway and a portion of the breath is guided along the secondary pathway. The remainder of the exhaled breath, which does not enter the secondary pathway, exits the device via the outlet of the primary pathway. If the device is to be used for collection of inhaled breath also, when a subject inhales through the device, the inhaled breath fills the primary pathway and a portion of the breath is guided along the secondary pathway. The remainder of the inhaled breath, which does not enter the secondary pathway, is inhaled by the user. In such way, both the inhaled and exhaled breaths may be analysed. In one embodiment, the secondary pathway is connected to the primary pathway at a branching point by a T-connector. In another embodiment, the T-connector forms part of the primary pathway and part of the secondary pathway itself.

In some embodiments, the sample of the exhaled breath to be guided along the secondary pathway is taken from the near to the periphery of the primary pathway. At the periphery of the primary pathway, the exhaled breath passing along it is less turbulent; sampling from here is preferred as it minimises turbulence in the secondary pathway and thus provides a constant flow rate in the secondary pathway, allowing more accurate sensor measurements.

In other embodiments, the sample of breath is not taken from the periphery of the primary pathway. For example, the sample may be taken from the centre of the primary pathway.

The outlet of the secondary pathway may be to the atmosphere outside of the device, or it may be an outlet to another part of the device or to another breathing apparatus used by the patient. This could be a breathing apparatus of an intensive care unit, for example, where metabolism may be monitored because patients could suffer from malnutrition.

The device comprises a flow sensor located between the inlet of the primary pathway and the branching point or between the branching point and the primary pathway outlet. The flow sensor is arranged to allow measurement of the gas flow in the primary pathway. Preferably, the flow sensor is the only sensor of the device that is located in the primary pathway and all the other sensors, discussed below, are located in the secondary pathway.

When the breath of the user is exhaled into the primary pathway of the device, the flow sensor measures the flow rate of the breath, preferably in mL/min. Preferably, the flow sensor measures instantly the entire flow of the exhaled breath. The flow sensor may be a hot film anemometer, a micro-thermal conductivity detector, a thermal sensor element, a thermal mass flow sensor, an ultrasonic transit time flow meter or any other appropriate sensor that can sense rapidly the flow rate of a gas mixture. When the branching point is before the flow sensor, the flow measurement may take into account the change in flow due to the secondary constant sampling flow.

The presence of a flow sensor which measures on a constant basis also allows the device to be used as a spirometer. Spirometry is the most common lung function test, which involves measurement of the volume of air inspired and expired by the lungs when a patient blows into a spirometer.

The device comprises an oxygen sensor arranged in the secondary pathway to take measurements of the exhaled breath in that pathway. The oxygen sensor may be an electrochemical partial pressure oxygen sensor, a paramagnetic oxygen sensor, fuel cell technology oxygen sensor, a light sensor that uses the fluorescence quenching properties of dye (e.g. a ruthenium based dye), a thermal conductivity detector (preferably a micro-thermal conductivity detector) (as described further below), a metal oxide semiconductor sensor, a polymer sensor or any other sensor type that is able to sense oxygen. A sensor with a response rate in the range of milliseconds is especially beneficial in the device of the invention.

A carbon dioxide sensor is also present in the device, and is also arranged in the secondary pathway to take measurements of the exhaled breath in that pathway. The carbon dioxide sensor may be a non-dispersive infrared sensor (NDIR) that uses the strong and unique infrared absorption of the carbon dioxide in a gas mixture, a metal oxide semiconductor sensor, a solid state sensor that uses a potentiometric measurement, a thermal conductivity detector (preferably a micro-thermal conductivity detector (as described below)), a polymer sensor or any other carbon dioxide sensor. A carbon dioxide sensor with high accuracy and low-response time is especially beneficial in the device of the invention.

The presence of a carbon dioxide sensor also means that the device may be used for capnography. Capnography is the monitoring of the concentration or partial pressure of carbon dioxide, and is used in cases of anaesthesia and to monitor the health relating to breathing problems such as asthma, COPD etc. The device is suitable for capnography because it is able to provide real-time carbon dioxide profiles of a patient's exhaled breath. It measures the partial pressure of carbon dioxide in the exhaled breath, and the fast response of the sensors provide information about the entire waveform of the exhaled carbon dioxide cycle (the so-called capnogram). For use as a capnograph, the device of the invention need not contain an oxygen sensor. In this case, the device of the invention is a portable breath analysis device comprising a primary gas flow pathway for passage of exhaled breath from an inlet to an outlet; a secondary gas flow pathway branched from the primary pathway at a branching point between the inlet and the outlet, the secondary pathway also having an outlet; a flow sensor between the inlet of the primary pathway and the branching point and arranged to allow measurement of the gas flow in the primary pathway; and a carbon dioxide sensor, wherein the carbon dioxide sensor is arranged in the secondary pathway to take measurements of the exhaled breath in that pathway.

As mentioned above, either the oxygen or the carbon dioxide sensor of the device may be a thermal conductivity detector, preferably a micro-thermal conductivity detector. This type of sensor is known for its low response time but lacks on selectively detecting oxygen or carbon dioxide in a three gas mixture such as 99% of the human breath ($O_2$, $N_2$, $CO_2$). A micro-thermal conductivity detector measures the thermal conductivity of the gas mixture. Thus if the precise concentration of two of the gases in a three gas mixture is known, then a measurement of the thermal conductivity of the three gas mixture allows the concentration of the third gas component to be calculated. In the case of the human breath the concentration of nitrogen is always constant at 78.08% whereas the concentrations of oxygen and carbon dioxide vary. Thus, if the oxygen concentration is measured by a selective oxygen sensor as described above, and it is known that nitrogen with a concentration of 78.08% is always present in the exhaled human breath, the thermal conductivity of the three gas mixture (nitrogen, oxygen, carbon dioxide) of the exhaled breath can be used to calculate the concentration of carbon dioxide. The same holds when carbon dioxide is measured with a sensor that selectively measures carbon dioxide and the signal of the thermal-conductivity detector is used to calculate the oxygen of the exhaled breath. Thus, a thermal-conductivity detector can be used as the sensor of either oxygen or carbon dioxide.

In some embodiments, the oxygen sensor may be positioned upstream of the carbon dioxide sensor in the secondary pathway. In alternative embodiments, the carbon dioxide sensor may be positioned upstream of the oxygen sensor.

In some embodiments, the oxygen and carbon dioxide sensors may be separate components. In alternative embodiments, the oxygen and carbon dioxide sensors may be combined as a single unit sensor, capable of sensing both oxygen and carbon dioxide. For example, an array of carbon nanotubes (CNTs) can be used for the simultaneous detection of oxygen and carbon dioxide among other breath biomarkers. In this case the oxygen and carbon dioxide sensor are combined in one array of carbon nanotubes (CNT's).

A subject may use the breath analysis device of the first embodiment by holding it in his hands and exhaling from his mouth into the device, via a mouthpiece or facemask when present. When a user exhales into the device, the exhaled breath passes along the primary pathway, where its flow rate is measured by the flow sensor, and a small fraction of the breath is guided to the oxygen and carbon dioxide sensors located in the secondary stream where measurements are taken.

In some preferred embodiments, the device is an indirect calorimeter. Indirect calorimetry is used to measure the human metabolism based on the amounts of $O_2$ and $CO_2$ that are found in the exhaled human breath.

In some preferred embodiments, devices of the invention comprise a dehumidifying means for reducing the humidity of an exhaled breath passing through the device. The dehumidifying means is positioned in the primary or secondary pathway between the inlet and the oxygen and carbon dioxide sensors. It is known that the exhaled breath has a high relative humidity (often up to 100% RH) and this can lead to condensation forming in the sensors. The sensors used are less accurate under condensed conditions and this is why the relative humidity of the breath is preferably reduced prior to passage across the sensors.

In some embodiments, an upstream portion of the secondary pathway comprises the dehumidifying means. Alternatively, or in addition, a portion of the primary pathway may comprise one or more dehumidifying means.

In one preferred embodiment, the dehumidifying means is a Nafion® tube. A Nafion® tube is used to dry the exhaled human breath. The exhaled breath is dried as it passes through a series of one or more Nafion® tubes along the primary and/or secondary pathways and reaches the humidity of ambient air. Nafion® is a registered trademark of E.I. duPont Company and refers to a copolymer of perfluoro-3, 6-dioxa-4-methyl-7-octene-sulfonic acid and tetrafluoroethylene.

Alternative means of dehumidifying the breath may also be used, instead of or in addition to a Nafion® tube. For example, in some embodiments, a chamber containing a wet sponge may be located along the secondary pathway in-line with a further chamber containing one or more chemical substances with the ability to absorb moisture and reduce humidity. Such chemicals may be chosen from, but are not limited to: magnesium perchlorate, Sodium chloride (halite) (NaCl), Calcium chloride (CaCl2), Sodium hydroxide (NaOH), sulfuric acid (H2SO4), Copper sulphate (CuSO4), phosphorus pentoxide (P2O5 or more correctly P4O10), silica gel, hydrated salts such as Na2SO4.10H2O, LiBr, LiCl and amines. In such embodiments, the exhaled breath will pass first through the wet sponge where its humidity may rise, and it will then be dried after passing through the chamber of the silica gel, calcium chloride and/or magnesium perchlorate etc. In the case of the inhaled air, its humidity will be increased significantly when it passes through the wet-sponge chamber and it will get dried after passing through the chamber with the chemical compounds (silica gel, calcium chloride, magnesium perchlorate etc.). This combination of a wet sponge, which ensures that both inhaled and exhaled breath is the same humidity before being dehumidified, and the dehumidifying chemical substance ensures that both inhaled and exhaled breath will have the same relative humidity when they reach the sensors, enhancing the accuracy with which their measurements can be compared given that they will not be affected by humidity differences.

The dehumidifying chamber containing chemicals may comprise a valve at its inlet and/or a valve at its outlet. Having a valve at both the inlet and the outlet of the dehumidifying chamber would allow the chamber to be closed off when the device is not in use, to prevent ambient air contacting the chemicals and thus prolong the lifetime of the chemicals.

In some embodiments, only the chamber with the chemical compounds could be used (silica gel, calcium chloride, magnesium perchlorate etc.) for drying the breath. In some embodiments, a combination of a Nafion® tube, a wet sponge and a chamber with chemical compounds (silica gel, calcium chloride, magnesium perchlorate etc.) may be used. In some embodiments a combination of a Nafion® tube and only the chamber with the chemical compounds could be used, without a wet sponge. In some embodiments, only a wet sponge and the chamber of chemical compounds could be used, only the chamber of chemical compounds, or only the Nafion® tube.

In alternative embodiments, a dehumidifying means is not present. The sensors may, for example, instead be heated to avoid condensation forming.

In some embodiments, the device comprises a dehumidifying means and the sensors are heated.

In some embodiments, a facemask or mouthpiece is connected to the inlet of the primary pathway, and, while the flow sensor and primary pathway remain in proximity to the mouthpiece or facemask, a length of tubing may form the portion of the secondary pathway extending from the branching point. In this way, the remainder of the device at the end of the long tube opposite the facemask, flow sensor and primary pathway may be kept, for example, in a pocket, bag or otherwise strapped to the user, whilst the user is using the device. The facemask may be strapped to the head of the user. In some embodiments, the tubing may comprise the dehumidifying means, for example if the tubing comprises a Nafion® tube drying mechanism. Such embodiments may be used in VO2 max testing, anaerobic threshold identification and several others fitness applications.

In some embodiments, the device comprises a pump for drawing exhaled breath through the secondary pathway. The pump regulates the flow rate through the secondary pathway to ensure a constant steady flow. The pump operates at a constant flow, drawing through the secondary pathway either a sample of the exhaled breath when it fills the primary pathway, or of the ambient air via the outlet of the primary pathway in the dead time between breath exhalations. Measurements of ambient air can be useful for calibration of the device.

One particularly preferred type of pump for use in devices of the invention is a rotary vane pump, since it can produce a steady flow without causing any turbulence, which is advantageous for accurate measurement by the sensors.

In alternative embodiments, the device does not comprise a pump. In such an embodiment, the gas flow may instead be controlled by the diameter and configuration of the gas flow pathways. For example, tubes of smaller diameter may be used along the gas flow pathways to reduce the flow rate of the exhaled breath as it passes through them.

In some embodiments, the device further comprises a valve system located between the branching point and the oxygen and carbon dioxide sensors. The valve system partitions the secondary pathway into an upstream portion between the branching point and the valve system and a downstream portion between the valve system and the outlet of the secondary pathway. The components of the valve system are moveable between at least a first position and a second position. The valve system has a valve outlet. The valve system may comprise one or more individual valves, and the valve system is at least a three-way valve system. In the first position, the components of the valve system are arranged such that the upstream portion of the secondary pathway is in fluid connection with the downstream portion of the secondary pathway; and in the second position, the components of the valve system are arranged such that the upstream portion of the secondary pathway is in fluid connection with the valve outlet and not with the downstream portion of the secondary pathway.

The valve system allows the device to select which exhaled breaths will be analysed by the sensors in the secondary pathway, and thus allows the device to operate in multiple modes. The different modes of operation allow the measurement of the consumed oxygen and produced dioxide of the user independently of his breathing rate.

The valve system regulates the modes of operation of the device. When the valve system pump is constantly in the first position (i.e. open), the sample of exhaled breath drawn down the secondary pathway continues through the valve system to the network of sensors, including carbon dioxide and oxygen sensors, in order to be analysed. When the valve system is in the second position (i.e. closed), the exhaled breath samples are guided to the valve outlet. In this way, the valve system regulates if a sample of a particular exhaled breath will be analysed or if it will be guided to the valve outlet to exit the device. This makes it possible for the device to be selective about which exhaled breaths are analysed, which is a very advantageous feature as it allows the device to be used in a variety of situations. For example, when the user is at rest and his breathing rate is not very high (for example, approximately 15 breaths per minute), the device is able to analyse the exhaled breath on a breath-by-breath basis, as the valve system will remain open and allow every exhaled breath to pass through it to the sensors. However, when the user is exercising intensely and his breathing rate is much higher (for example, approximately 40-50 breaths per minute), the response time of the sensors may be insufficient to accurately measure two successive breaths for breath-by-breath analysis. Thus, in the case of a high breathing rate a different mode of operation of the device may be employed where not every breath is analysed: for example, every second, every third, every fourth or even fewer breaths may be analysed. In this way, the valve system compensates for possible short-comings in the response time of the sensors used in the device. Preferably, the valve system is electrically operated for this purpose.

In some embodiments, the valve system is positioned downstream of the pump on the secondary pathway. Alternatively, the valve system may be upstream of the pump. Alternatively, the pump and the valve system may be integral to one another.

Preferably, devices of the invention comprise a micro-controller.

The micro-controller may be used to power the pump when the pump is supplied with power from the micro-controller. The micro-controller also carries out the data processing of the device: the flow-rate sensed by the flow sensor, the concentration of oxygen measured in the exhaled breath by the oxygen sensor, and the concentration of carbon dioxide sensed by the carbon dioxide each create an electrical signal that is communicated to the micro-controller. The microcontroller controls the valve system and the modes in which it operates. The microcontroller can be arranged so as to alter the mode of operation depending on the breathing rate as measured by the flow sensor.

The flow rate measured by the flow-sensor is translated to an electrical signal which is fed to the micro-controller of the device, which accordingly determines the mode of operation of the device by controlling the valve system as described above. The flow rate measurement from the flow-sensor is supplied to the microcontroller and allows the microcontroller to determine the breathing frequency (breathing rate) through a custom built algorithm. Depending on the breathing frequency measured, and by the micro-controller controls the valve system to determine whether the device will analyse the user's exhaled breath on a breath-by-breath basis or not (e.g. every second breath will be analysed instead, or every third breath etc.), i.e. selects which mode the device operates in. By synchronising the flow sensor with the electronically operated valve system in this way, the expired breath sample is then guided either to the sensors in the secondary pathway or to the valve outlet to exit the device.

In some embodiments, the device further comprises a one-way (non-rebreathing) valve positioned between the inlet and the flow sensor, through which gas may pass in a direction from the inlet to the flow sensor only.

Where a non-rebreathing valve is used, it may be present for example in a mouthpiece or a facemask of the primary pathway. In this case, the user must inhale through the nose and exhale through the mouth.

Alternatively, the one-way valve may be absent. In this case, the user may inhale and exhale from his mouth while his nose is closed with a nose-clip. In situations where inhaling and exhaling needs to be done through the mouth and this can be achieved by using a mouthpiece or facemask without a non-rebreathing valve.

In some embodiments, the secondary flow pathway includes a barometric pressure sensor, a relative humidity sensor and/or a temperature sensor. The signals of these sensors may be communicated to the micro-controller in order to compensate for changes in the ambient barometric pressure, relative humidity and temperature. These signals enable the readings of the oxygen and/or carbon dioxide sensors to be converted accurately into readings of the concentration of the gases in the exhaled breath. The also facilitate the usage of the device in any condition of humidity, any altitudes and in different climates.

The barometric pressure sensor, relative humidity sensor and/or temperature sensor may be arranged to take measurements in the primary pathway or in the secondary pathway. Preferably, they are arranged to take measurements in the secondary pathway.

In some embodiments, one or more further sensors may be present. For example, one or more of an acetone, nitric oxide, sulphur compounds, pentane, ethanol and hydrocarbons sensor may be present in the device.

If an acetone sensor is added to the device, the glucose level of a patient can be monitored in a non-invasive way. This is particularly interesting for patients that are diabetic since they need to monitor their glucose level on a day-to-day basis. It is known that the level of acetone concentration that is found in the exhaled breath is correlated to the blood glucose level. However, it is extremely difficult to determine the baseline of an individual's glucose level. In this device, by combining the information gathered about the metabolism level of an individual and/or his respiratory quotient (RQ) with the concentration of acetone that is found in his exhaled breath, it is possible to determine the baseline level by a suitable algorithm.

If a nitric oxide sensor is added to the device of the invention the device can provide information regarding the user's asthma medication. The nitric oxide levels that are found in the breath can give to a physician information about the effectiveness and the dose needed for the asthmatic patient, which can be used to regulate the medication for an asthma patient.

If a sensor that measures sulphur compounds and/or hydrocarbons is added to the device, then information about mouth hygiene and information about mouth odour can be provided to the user of the device.

If a pentane sensor and an ethanol sensor is added to the device, then oxidative stress can be measured.

The one or more further sensors may be arranged to take measurements in the primary pathway or in the secondary pathway. Preferably, they are arranged to take measurements in the secondary pathway.

A sampling chamber may be present, positioned between the oxygen and carbon dioxide sensors and the outlet of the secondary pathway. One or more further sensors, which may include the sensors discussed above, may be in fluid connection with the interior of the sampling chamber, for analysing the collected breath. The sampling chamber may have a volume in the range of mL.

The sampling chamber may be formed as part of the secondary pathway, in line with the outlet of the secondary pathway, such that exhaled breath passes through the sampling chamber before exiting the device through the secondary pathway outlet. Alternatively, the sampling chamber may be in fluid connection with the secondary pathway by way of a sampling chamber pathway branched from the secondary pathway. In this way, all or only a sampled fraction of exhaled breath passing along the secondary pathway towards the secondary pathway outlet enters the sampling chamber.

Where a valve system is present as discussed above, the valve system may be configured such that the sampling chamber samples only exhaled breath. The flow sensor may detect and differentiate between inhaled and exhaled breath, and thus send the necessary signal to the valve system to guide inhaled breaths to the valve outlet and exhaled breaths onwards to the sampling chamber.

In some preferred embodiments, the device comprises a communication means for communication between the microcontroller and a mobile phone or other external device. For example, the communication means may be a Bluetooth connection via the microcontroller, to enable communication with a mobile phone. The device may be used for remote medical monitoring. The communication means allows data collected by the microcontroller to be sent directly to a remotely located device, for example via the internet. Data collected may be displayed on a computer or, for example, a smartphone application. Alternatively or in addition, a communication means may be a USB connector, a removable memory card, a cable, a wireless unit, an Ethernet shield, or a mobile broadband unit, for example.

The operation of a device of the invention as an indirect calorimeter is based on the determination of the oxygen consumption, carbon dioxide production and the flow rate that can be determined by the exhaled breath of the user. In a preferred embodiment, when a subject exhales into the device, the exhaled breath fills the primary pathway. Upon entering the primary pathway, the entire flow rate of the expired breath is preferably instantly measured. Similarly, upon inspiration, the gas that forms the inspired breath may be analysed.

The exhaled human breath consists mainly (~99%) of nitrogen, oxygen and carbon dioxide. The Haldane transform assumes that nitrogen is physiologically inert. This means that the volume of inspired nitrogen must be the same with the volume of expired nitrogen.

This can be seen from the following equations:

$$V_I F_I N_2 = V_E F_E N_2 \Rightarrow V_I = V_E \frac{F_E N_2}{F_I N_2} \tag{1}$$

$$F_E N_2 = 0.99063 - (F_E O_2 + F_E CO_2) \tag{2}$$

$$F_I N_2 = 0.7808 \tag{3}$$

$$V_I = V_E \frac{0.99063 - (F_E O_2 + F_E CO_2)}{0.7808} \tag{4}$$

where:

$V_1$=Inhaled flow rate $V_E$=Exhaled flow rate $F_E N_2$=Fraction of expired nitrogen $F_1 N_2$=Fraction of inspired nitrogen $F_E O_2$=Fraction of expired oxygen $F_E CO_2$=Fraction of expired carbon dioxide Equation 1 describes that nitrogen is inert and the volume of inspired nitrogen is equal to the volume of the expired nitrogen which is the Haldane approximation. Equation 2 describes that the fraction of exhaled nitrogen equals to the 99.063% of the exhaled breath minus the fraction of expired oxygen and carbon dioxide. Equation 3 describes that the fraction of inspired nitrogen equals to 78.08%, which is the percentage of nitrogen in ambient air. Equation 4 is the equation used to calculate the inspired flow rate when the expired flow rate, the fraction of expired oxygen and the fraction of expired carbon dioxide are known from the various sensors in the device.

After entering the primary pathway (in which the flow rate of the expired, and optionally inspired, breath is measured), a portion of the breath is guided along the secondary pathway. This may be assisted by the presence of a pump in the secondary pathway to draw sample with a constant flow-rate down the secondary pathway as described above. The remainder of the exhaled breath, which does not enter the secondary pathway, exits the device via the outlet of the primary pathway. Inhaled breath which does not enter the secondary pathway is inhaled by the user.

Along the secondary pathway, the expired breath passes through a series of Nafion® tubes, which reduces the humidity of the exhaled breath. The relative humidity of the exhaled breath is reduced through the Nafion® tube until it reaches the ambient relative humidity. Alternatively or in addition, the sensors may be heated to prevent condensation of humid breath on them.

This flow rate measurement from the flow-sensor is supplied to the microcontroller and allows the microcontroller to determine the breathing frequency (breathing rate) and to control the valve system accordingly, as described above.

Once a sample of expired breath has passed through the valve system and has not been expelled via the valve outlet, it continues to the network of sensors of the device. In a preferred embodiment, the sensor network of the device includes a flow sensor, an oxygen sensor, a carbon dioxide sensor, a temperature sensor, a barometric pressure sensor and a humidity sensor. The temperature sensor, barometric pressure sensor and the humidity sensors are used to compensate the measurements of the oxygen and carbon dioxide sensors.

When the oxygen and carbon dioxide sensors measure the human breath, they create a periodic signal that resembles a function describing a wave. In one method of operation of the device, the two waveforms, the waveform of the oxygen ($f_{O2}$) and the waveform of the carbon dioxide ($f_{CO2}$) are sensed and then refitted by a customised built algorithm that is based on the following equation:

$$f_{O_2}(t)=-f_{CO_2}(t)*c1+c2 \tag{5}$$

where c1 and c2 are positive constants.

A human's energy expenditure is divided into resting metabolic rate (RMR), physical activities and thermogenesis that is induced by food intake. The device is able to measure the oxygen consumed and the carbon dioxide produced by an individual. By determining the instant flow of the exhaled breath and the fraction of expired oxygen $F_EO_2$ as well as the fraction of expired carbon dioxide $F_ECO_2$, the resting energy expenditure (REE) or resting metabolic rate (RMR) in kCal/day of an individual can be calculated through the Weir equation.

$$REE=1.44[3.9(VO_2)+1.1(VCO_2)] \tag{6}$$

$$VO_2=V_1F_1O_2-V_EV_EO_2 \tag{7}$$

$$VCO_2=V_1F_1CO_2-V_EF_ECO_2 \tag{8}$$

where $V_1$=Inhaled flow rate $V_E$=Exhaled flow rate $F_1O_2$=Fraction of inspired oxygen $F_1CO_2$=Fraction of inspired carbon dioxide $F_EO_2$=Fraction of expired oxygen $F_ECO_2$=Fraction of expired carbon dioxide The inhaled flow rate is calculated by equation (4), as described previously. The fraction of inspired oxygen ($F_1O_2$) is constant at 0.2005 since it is the fraction of inspired oxygen from ambient air. Similarly, the fraction of inspired carbon dioxide ($F_1CO_2$) is constant at 0.00039 since it is the fraction of inspired carbon dioxide from ambient air. Thus, the energy expenditure of an individual is calculated by measuring the exhaled flow rate ($V_E$), the fraction of inspired oxygen ($F_EO_2$) and the fraction of inspired carbon dioxide ($F_ECO_2$).

Apart from the energy expenditure of an individual, it is possible to measure his respiratory quotient that is defined as:

$$RQ=\frac{VCO_2}{VO_2} \tag{9}$$

The respiratory quotient (RQ) is usually between 0.6-1.0 for aerobic metabolism. When the RQ is closer to the value of 0.7, the user of the device is metabolising fat. Whereas, when the RQ is closer to the value of 1.0, the user is metabolising carbohydrates. The medium value of RQ=0.8 shows that the user is metabolising protein.

In addition to metabolism by indirect calorimetry, various other functions may be measured by the device. These include, but are not limited to, the calories burned during exercise, in which instance a facemask may be used as part of the primary pathway to facilitate use of the device while exercising. The device may also be used to calculate body mass index (BMI, a measure of the fat-free mass of an individual), may track the history of the user with corresponding software (such as a smartphone application) to draw conclusions about the health status of the user, may be used as a capnometer and/or may be used as a spirometer.

The operation of the device is conducted through the micro-controller and the data measured can be transmitted to a smartphone or computer for example.

According to another aspect of the invention, there is provided a portable breath analysis device comprising: a primary gas flow pathway for passage of exhaled breath from an inlet to an outlet, a secondary gas flow pathway branched from the primary pathway at a branching point between the inlet and the outlet, the secondary pathway also having an outlet; and a flow sensor between the inlet of the primary pathway and the branching point and arranged to allow measurement of the gas flow in the primary pathway. These features are as described above. The device of this aspect also comprises at least one sensor in for a gas. The device further comprises the valve system whose components are movable between at least a first position and a second position, as described above, which selectively allows breaths to pass through to the sensors to provide different "modes" of the device. The valve system comprises a valve outlet, and the valve system is located between the branching point and the at least one sensor, and partitions the secondary pathway into an upstream portion between the branching point and the valve system and a downstream portion between the valve system and outlet of the secondary pathway.

The at least one sensor is arranged to take measurements in the downstream portion of the secondary pathway, as described above.

The device of the second aspect of the invention may include a carbon dioxide sensor. The device may also or alternatively comprise an oxygen sensor. Both of these sensors can be as described above.

Preferably, the device comprises both a carbon dioxide sensor and an oxygen sensor and is an indirect calorimeter, to allow a user to use the device for the monitoring of their metabolism, as described above.

All further features described above for the first aspect of the invention may be present in the second aspect. In particular, the device according to the second aspect may comprise, for example, a pump, a one-way valve in the primary pathway, a humidity sensor, a temperature sensor, a pressure sensor, one or more further sensors, a microcontroller and/or a communication means for communication between the microcontroller and a mobile phone or other external device.

According to a third aspect of the invention, there is provided a method of analysing exhaled breath of a subject comprising the step of the subject breathing into a breath analysis device of the invention, as described above. A method of analysing gas that forms an inhaled breath of a subject comprising the step of the subject inhaling through a breath analysis device of the invention is also provided.

Example 1

An example of a device according to the invention is shown schematically in FIG. 1. The device comprises a mouthpiece 1 connected to a flow sensor 2. Flow sensor 2 measures the flow rate of exhaled and inhaled breath when a user exhales and inhales into the mouthpiece. In the device shown, a non-rebreathing valve is not present; a user may inhale as well as exhaling into the device. When inhaling, ambient air is drawn through the outlet at the end of the primary pathway. Air may thus pass through the primary pathway in two directions.

The primary pathway 16 is formed of the mouthpiece 1, the flow sensor 2, and part of a T-shaped connector 3 which joins the primary pathway to the secondary pathway 14. The T-shaped connector also forms part of the secondary pathway. A portion of the exhaled breath is sampled from the periphery of the primary pathway and is guided along the secondary pathway.

The sample of exhaled breath is drawn through the secondary pathway at a constant flow rate by a micro-pump 5 present in the secondary pathway. When no breath is being exhaled, the pump instead draws ambient air into the pathway, through the outlet of the primary pathway.

As the breath sample is drawn through the secondary pathway, it passes through a Nafion® tube 4 which forms part of the secondary pathway (in the upstream portion 14*a* of the secondary pathway). This reduces the humidity of the exhaled breath before it reaches the sensors.

The measurements from the flow sensor 2 are delivered to the micro-controller 12, where the breathing rate of the user is determined. Depending on the breathing rate, the micro-controller 12 operates the three-way valve system 6 to allow all exhaled breath samples to continue to the subsequent network of sensors (in the downstream portion 14*b* of the secondary pathway), or only a subset of the exhaled breath samples. A given exhaled breath may pass through the three-way valve system 6 to continue along the secondary pathway to the sensors, or may be expelled through a the valve outlet 15, depending on the arrangement of the three-way valve system 6, as controlled by the micro-controller 12.

Those exhaled breath samples which do pass through the valve system 6 reach the sensors. The sensors include an oxygen sensor 7, a carbon dioxide sensor 8, a barometric pressure sensor 9, a relative humidity sensor 10, and a temperature sensor 11. One or more additional sensors 13 are also present, for example one or more sensors selected from the group consisting of acetone, nitric oxide, sulphur compounds and hydrocarbon sensors.

The measurements from each of the sensors are translated into electrical signals which are delivered to the microcontroller, which conducts the data processing of the device.

Figure 2:
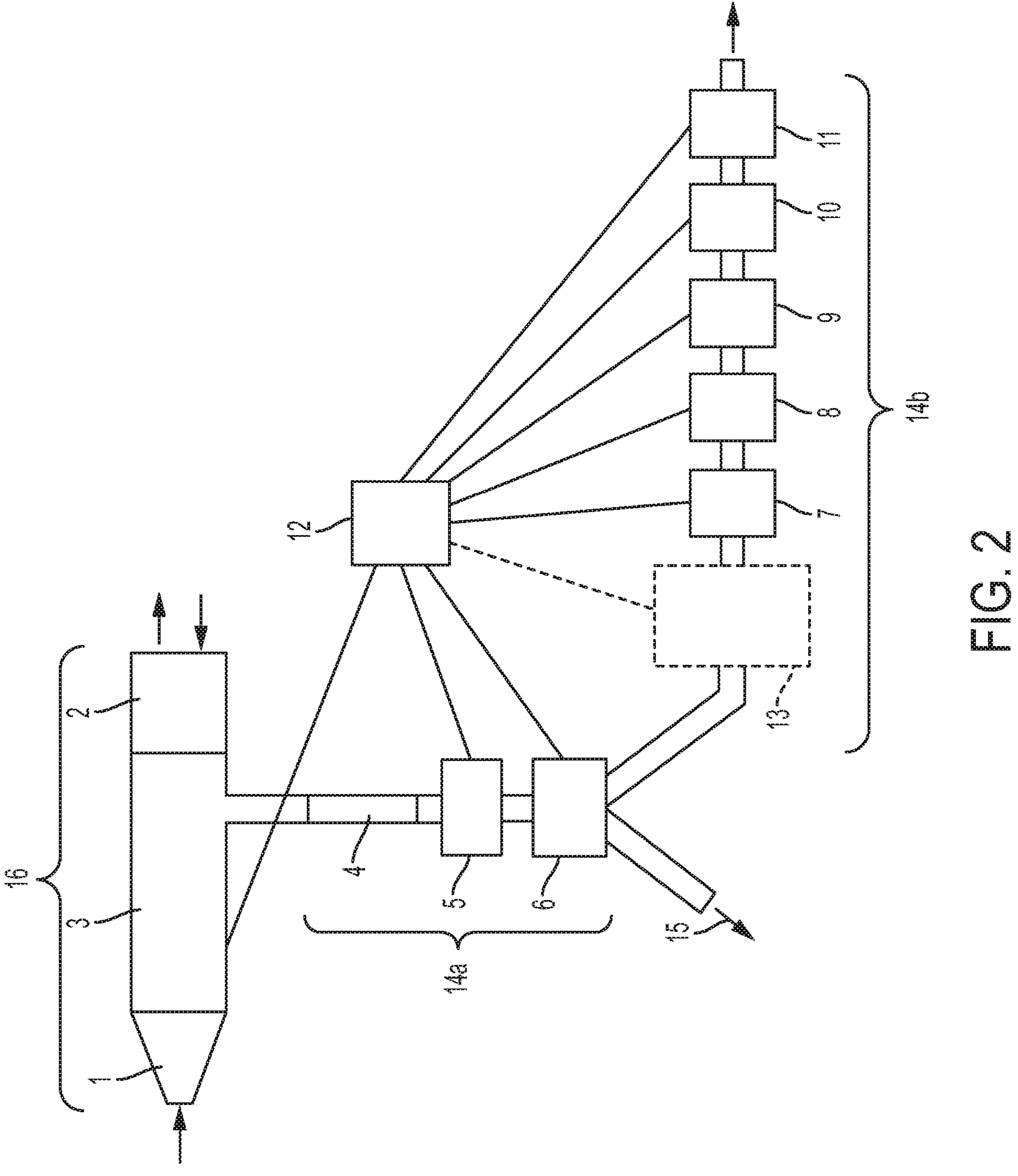
FIG. 2 shows a schematic diagram of a second embodiment of the invention.

An example of a device according to a second embodiment of the invention is shown in FIG. 2. In the device of FIG. 2, all components are the same except that the flow sensor 2 is located on the primary pathway between the branching point with the secondary pathway and the primary pathway outlet, rather than between the inlet and the branching point.

Example 2

Time Data

Figure 3:
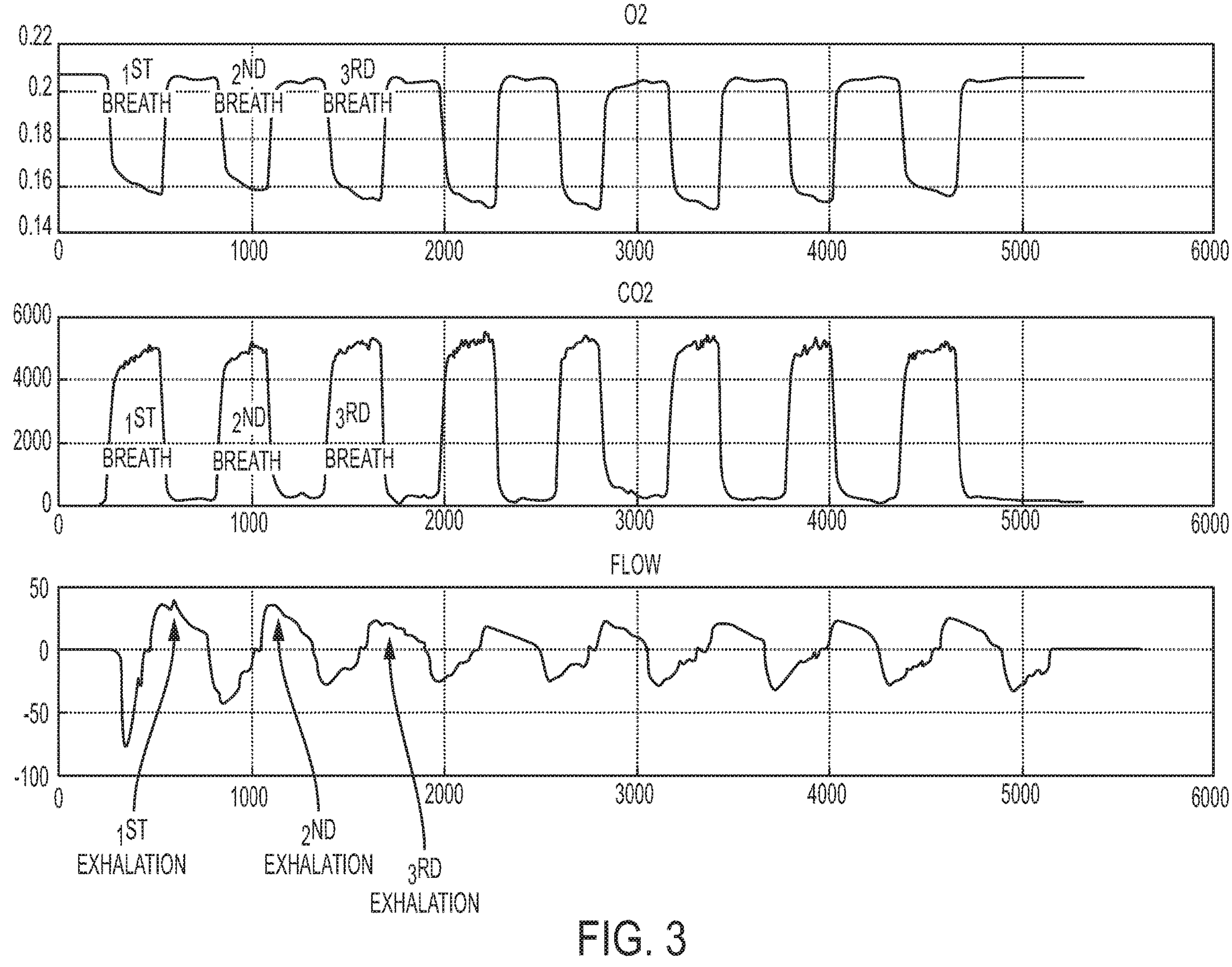
FIG. 3 shows three plots over time (in seconds) of the oxygen, carbon dioxide and flow measurements obtained by a device of the invention on a breath-by-breath basis. Oxygen is measured in $O_2$ (%), carbon dioxide is measured in ppm and flow is measured in L/min.

Plots over time (in seconds) of the oxygen, carbon dioxide and flow measurements obtained by a device of the invention on a breath-by-breath basis are shown in FIG. 3. Oxygen is measured in $O_2$ (%), carbon dioxide is measured in ppm and flow is measured in L/min.

Example 3

Clinical Validation of Device

Figure 4:
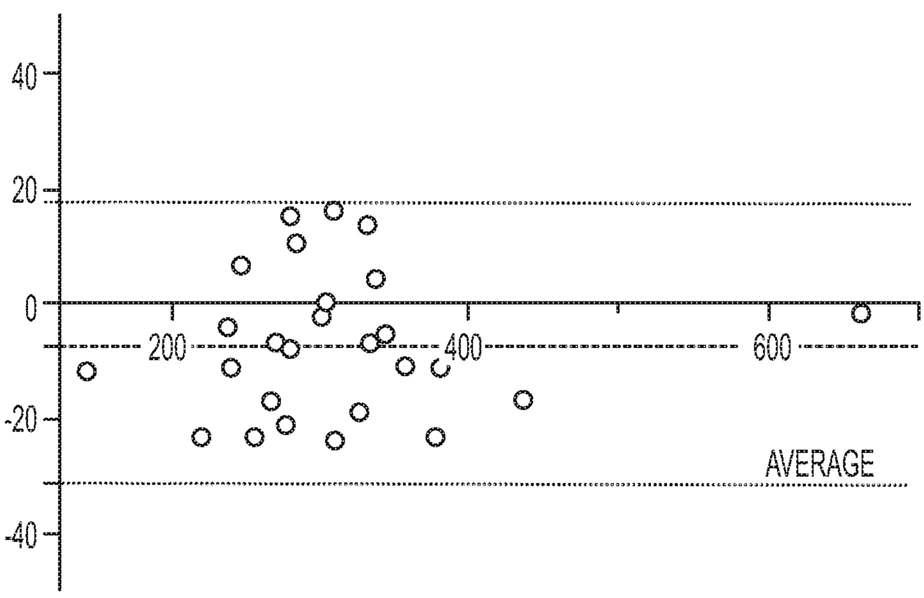
FIG. 4 shows a Bland-Altman plot showing the difference in measured $VCO_2$ values for a device in accordance with the present invention and a comparator gold-standard device.
Figure 5:
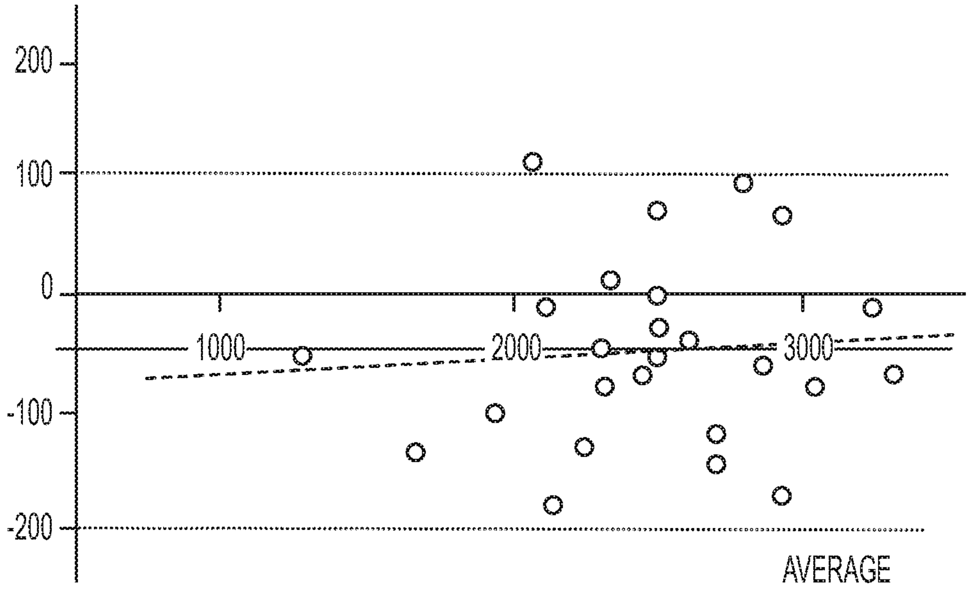
FIG. 5 shows a Bland-Altman plot showing the difference in measured energy expenditure values for a device in accordance with the present invention and a comparator gold-standard device.
Figure 6:
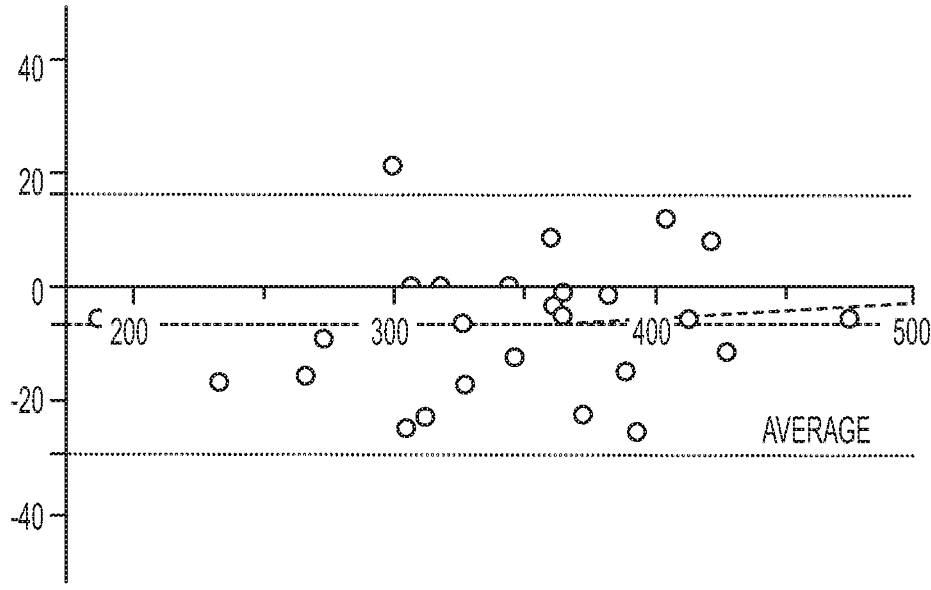
FIG. 6 shows a Bland-Altman plot showing the difference in measured $VO_2$ values for a device in accordance with the present invention and a comparator gold-standard device.

A device in accordance with the invention was validated in a clinical setting. Metabolism of 25 healthy subjects was measured simultaneously by a gold-standard device and by a device in accordance with the invention, in order to assess the accuracy of the device described herein. Values for $VCO_2$, $VO_2$ and energy expenditure were measured for each subject. FIGS. 4 to 6 show Bland-Altman plots which demonstrate the difference in the measured values of $VCO_2$ energy expenditure (EE) and $VO_2$, between a gold-standard metabolic assessment device and an indirect calorimeter device as described herein. From FIGS. 4 to 6 it can be concluded that the device according to the invention has medical grade accuracy according to the norms of the industry.

Whilst the present invention has been described and illustrated with reference to particular embodiments, it will be appreciated by those of ordinary skill in the art that the invention lends itself to many different variations not specifically illustrated herein. Where in the foregoing description, integers or elements are mentioned which have known, obvious or foreseeable equivalents, then such equivalents are herein incorporated as if individually set forth. Reference should be made to the claims for determining the true scope of the present invention, which should be construed so as to encompass any such equivalents. It will also be appreciated by the reader that integers or features of the invention that are described as preferable, advantageous, convenient or the like are optional and do not limit the scope of the independent claims. Moreover, it is to be understood that such optional integers or features, whilst of possible benefit in some embodiments of the invention, may not be desirable, and may therefore be absent, in other embodiments.

The invention claimed is:

1. A portable breath analysis device comprising:

a primary gas flow pathway for passage of exhaled breath from an inlet to an outlet;

a secondary gas flow pathway branched from the primary pathway at a branching point between the inlet and the outlet, the secondary pathway also having an outlet;

a flow sensor (i) positioned between the inlet of the primary pathway and the branching point or between the branching point and the outlet of the primary pathway and (ii) arranged to allow measurement of a gas flow in L/min in the primary pathway;

an oxygen sensor;

a carbon dioxide sensor;

a humidity sensor;

a temperature sensor; and a microcontroller;

wherein:

the device is an indirect calorimeter;

the oxygen sensor and the carbon dioxide sensor each have millisecond response rates and are arranged in-line in the secondary pathway to take breath-by-breath measurements of inhaled breath and exhaled breath from a subject in the secondary pathway;

the humidity sensor is configured to measure humidity of air in the secondary pathway;

the temperature sensor is configured to measure temperature of air in the secondary pathway;

the flow sensor, oxygen sensor and carbon dioxide sensor are heated to prevent formation of condensation;

the microcontroller is configured to:

receive measurements from the oxygen sensor, carbon dioxide sensor, the humidity sensor, and the temperature sensor; and compensate for changes in humidity and temperature and accurately determine readings for oxygen and carbon dioxide concentrations;

the flow sensor is a hot film anemometer or a micro-thermal conductivity detector;

the portable breath analysis device is wearable or holdable in the hands of the subject;

the secondary pathway comprises one or more tubes sized of smaller diameter than the primary pathway and configured to regulate flow rate through the secondary pathway; and the device does not include a pump, a valve system, or a dehumidifying means.

2. The portable breath analysis device of claim 1, wherein either the oxygen sensor or the carbon dioxide sensor is a thermal conductivity detector.

3. The portable breath analysis device of claim 1, further comprising one or more further sensors.

4. The portable breath analysis device of claim 1, further comprising one or more further sensors selected from the group consisting of acetone sensors, nitric oxide sensors, sulfur compound sensors, pentane sensors, ethanol sensors, and hydrocarbon sensors.

5. The portable breath analysis device of claim 1, wherein the device comprises a communication means for communication between the microcontroller and a mobile phone or other external device.

6. The portable breath analysis device of claim 1, wherein the device uses an algorithm based on the equation $$f_{O_2}(t)=-f_{CO_2}(t)*c1+c2 \quad (5)$$

wherein $f_{O_2}$ are $f_{CO_2}$ waveforms of oxygen and carbon dioxide respectively, as determined from the measurements of the oxygen and carbon dioxide sensors, and wherein c1 and c2 are positive constants.

7. The portable breath analysis device of claim 1, wherein the flow sensor measures expired breath flow rate, and wherein the device uses the equation $$V_I = V_E \frac{0.99063 - (F_E O_2 + F_E CO_2)}{0.7808}$$

to calculate inspired breath flow rate, where:

$V_I$=Inhaled flow rate $V_E$=Exhaled flow rate $F_E O_2$=Fraction of expired oxygen $F_E CO_2$=Fraction of expired carbon dioxide.

8. The portable breath analysis device of claim 1, wherein the oxygen sensor is a light sensor, wherein the light sensor uses the fluorescence quenching properties of a dye, and wherein the carbon dioxide sensor is a thermal conductivity detector.

9. The portable breath analysis device of claim 1, further comprising a pressure sensor.

10. The portable breath analysis device of claim 1, wherein the primary pathway is configured for passage of both inhaled and exhaled air.

11. The portable breath analysis device of claim 1, wherein the primary pathway comprises a facemask without a non-rebreathing valve.

12. The portable breath analysis device of claim 1, wherein the device is arranged so that a sample of breath to be guided along the secondary pathway is not taken from a periphery of the primary pathway.

13. The portable breath analysis device of claim 12, wherein the device is arranged so that the sample is taken from the centre of the primary pathway.

14. The portable breath analysis device of claim 1, wherein the flow sensor is positioned between the branching point and the outlet of the primary pathway.

15. A method of analyzing a breath of a subject, the method comprising: breathing, by the subject, into or from a portable breath analysis device according to claim 1 while the portable breath analysis device is held in the hands of the subject.

16. The method of claim 15, wherein the breathing comprises exhaling, by the subject, an exhaled breath into the portable breath analysis device.

17. The method of claim 15, wherein the breathing comprises inhaling, by the subject, an inhaled breath from the portable breath analysis device.

* * * * *